United States Patent [19]
Yoshinaga et al.

[11] Patent Number: 5,123,731
[45] Date of Patent: Jun. 23, 1992

[54] PARTICLE MEASURING DEVICE

[75] Inventors: Kazuo Yoshinaga, Machida; Moritoshi Miyamoto, Kawasaki, both of Japan

[73] Assignee: Canon Kabushiki Kaisha, Tokyo, Japan

[21] Appl. No.: 701,376

[22] Filed: May 13, 1991

Related U.S. Application Data

[63] Continuation of Ser. No. 302,412, Jan. 27, 1989, abandoned.

[30] Foreign Application Priority Data

| | | |
|---|---|---|
| Feb. 1, 1988 [JP] | Japan | 63-021502 |
| Jun. 15, 1988 [JP] | Japan | 63-147095 |
| Oct. 3, 1988 [JP] | Japan | 63-250252 |

[51] Int. Cl.$^5$ .................................................. G01N 21/64
[52] U.S. Cl. ........................................... 356/73; 250/461.2
[58] Field of Search .................. 356/73, 335, 338, 336; 250/461.2; 307/427

[56] References Cited
U.S. PATENT DOCUMENTS

| | | | |
|---|---|---|---|
| 3,826,364 | 7/1974 | Bonner et al. | 3/111.5 |
| 3,916,205 | 10/1975 | Kleinerman | 250/461.2 |
| 3,934,154 | 1/1976 | Cook | 307/427 |
| 4,131,800 | 12/1978 | Bruck et al. | 250/461.2 |
| 4,243,318 | 1/1981 | Stohr | 250/461.2 |
| 4,284,355 | 8/1981 | Hansen et al. | 250/461.2 |
| 4,284,412 | 8/1981 | Hansen et al. | 230 B/915 |
| 4,514,257 | 4/1985 | Karlsson et al. | 356/335 |
| 4,612,456 | 9/1986 | Gergely | 307/427 |
| 4,683,212 | 7/1987 | Uffenheimer | 356/73 |
| 4,847,198 | 7/1989 | Nelson et al. | 356/301 |

*Primary Examiner*—Richard A. Rosenberger
*Attorney, Agent, or Firm*—Fitzpatrick, Cella, Harper & Scinto

[57] ABSTRACT

A particle measuring device having a light source for irradiating particles to be examined, light wavelength convertor provided in the optical path of the a light source and at least emitting a light converted into the short wavelength side relative to the wavelength of the incident light from the light source, and photometer for photometering the light from the particles to be examined.

32 Claims, 8 Drawing Sheets

PARTICLE MEASURING DEVICE

This application is a continuation of application Ser. No. 302,412 filed Jan. 27, 1989, now abandoned.

BACKGROUND OF THE INVENTION

1. Field of the Invention

This invention relates to a particle measuring device, and more particularly to a device in which, for example, light is applied to separated individual particles to be examined and the optical reaction of the particles to be examined is detected to thereby analyze the nature, structure, etc. of the particles to be examined, or a device for optically measuring the condensation reaction of carrier particles such as sensitized latex and detecting an antigen or an antibody.

2. Related Background Art

Heretofore, in a particle measuring such as a flow cytometer, individual cells have been separated from one another by the method of flowing a high-speed layer flow outside a cell solution devised by Crosland Taylor, whereby it has become possible to obtain information about the individual cells, and much information can be obtained particularly by applying a light beam to the cells to thereby measure the scattered light thereof, and further dyeing particles to be examined in advance with a fluorescent dye and measuring the fluorescence excited and emitted by the application of the light beam. To obtain the scattered light or the fluorescence by minute cells with good accuracy, a light beam of great output which has little noise and is good in condensing property is necessary, and generally a laser light is used. Information such as the size and shape of cells, the diameter and volume of nucleus, and the complexity of the structure in the nucleus is obtained from the scattered light. From fluorescence, it is possible to find the amount of DNA and the amount of RNA by the dyeing of DNA and RNA. Particularly, by coupling the fluorescent coloring matter to an antigen or an antibody, causing it to react to the antigen or the antibody and measuring the fluorescence by a flow cytometer, quantitative measurement of a particular antigen or antibody on the surface of a cell becomes possible. In these cases, the light beam applied must be of a wavelength which excites the fluorescent coloring matter.

However, in the measurement of scattered light by the flow cytometer, the wavelength of the irradiating light has been uniform and new particle analysis data could not be obtained. Also, in fluorescence measurement, the irradiating light beam must be one which excites the fluorescent coloring matter, but the fluorescence coloring matter used is limited to fluorescein, rhodamine or umbelliferon. For these limited fluorescent coloring matters, a short wavelength gas laser such as $Ar^+$ laser (488 or 515 nm), $He-Cd^+$ laser (442 or 325 nm) or $N_2$ laser (337 nm) or a coloring matter laser excited by a short wavelength laser is used as an irradiating light beam. Such a short wavelength laser or a coloring matter laser becomes bulky when a great output is to be obtained, and also lacks in stability, and this has led to the disadvantage that a particle measuring device using it also is bulky and complex and lacks in stability.

Also, where a plurality of fluorescent coloring matters of different absorbing wavelengths are used at one time, if an exciting light of a single wavelength is used, the intensity of fluorescence will be remarkably reduced and in an extreme case, no fluorescence will be emitted. Therefore, it has been necessary to prepare a plurality of laser sources of wavelengths suitable for exciting the respective fluorescent coloring matters, but in such case, the device becomes more bulky and more expensive, and the optical system for irradiating particles to be examined also becomes complex. Devices of such a construction are described, for example, in U.S. Pat. No. 3,826,364 and U.S. Pat. No. 4,284,412.

Figure 15A:
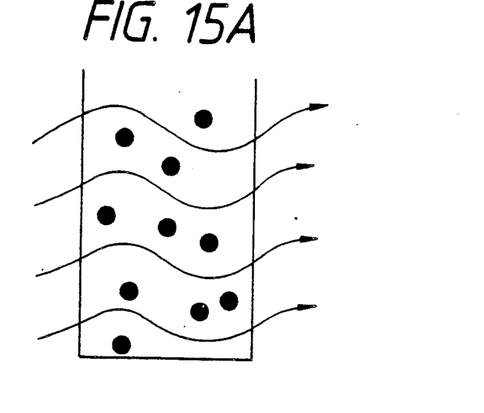
FIGS. 15A and 15B illustrate the principle of measurement of latex condensed lumps.
Figure 15B:
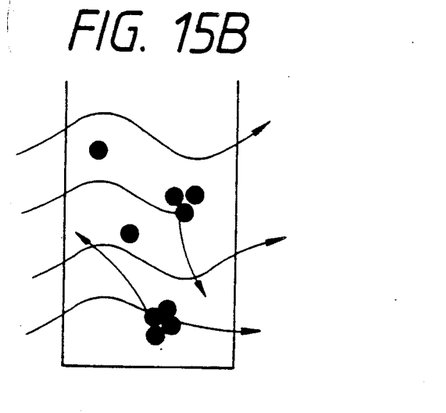

As another particle measuring device, there is known a device for measuring immunoreaction by the use of carrier particles such as latex. A suspension with a sample to be examined (for example, serum) including antigens or antibodies added to a suspension in which insoluble carrier particles (for example, latex particles) sensitized by a particular antibody or antigen are suspended at a predetermined concentration is prepared and an irradiating light is applied thereto. If at that time, the latex particles in the suspension are in their dispersed state, the light of much longer wavelength than the particle diameter is transmitted without being much affected by the presence of the latex particles, as shown in FIG. 15A of the accompanying drawings. That is, transmitted light of great intensity is obtained. However, when said sensitized latex particles are coupled together by the reaction of the antigen or antibody to form particle lumps of a large particle diameter and the particle diameter of the condensed particle lumps becomes approximate to the wavelength of the light, the light is scattered by the particle lumps as shown in FIG. 15B of the accompanying drawings and the intensity of transmitted light decreases. A reaction speed analyzing method of measuring and analyzing the concentration of the suspension from the reaction speed catching the variation in this intensity of transmitted light with time, and a reaction terminal analyzing method of measuring and analyzing the intensity of transmitted light or the intensity of scattered light in the suspension after the reaction terminates are generally known. Thereby, measurement of the amount of particular antigen or the amount of particular antibody in the sample to be examined has become possible and immunological diagnosis has been done.

Figure 13:
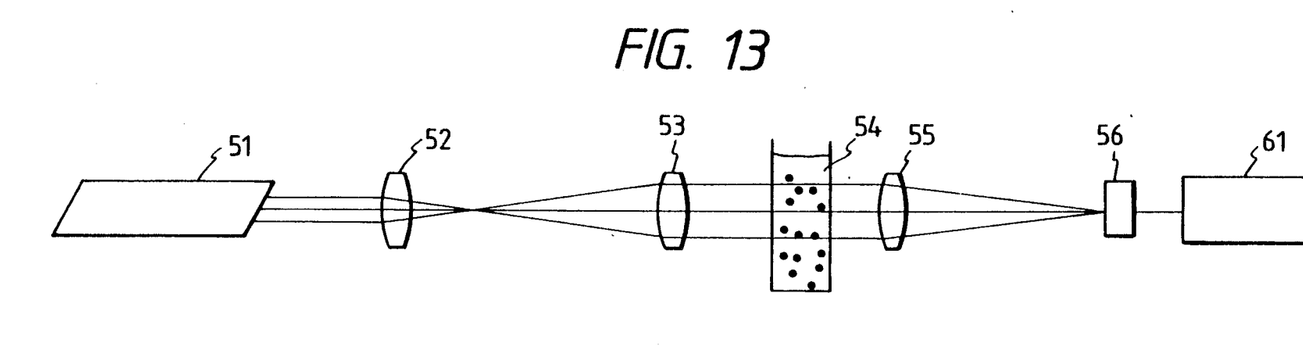
FIG. 13 shows the construction of a conventional particle measuring device using latex condensation.

As an example, a latex particle suspension of a predetermined concentration which is sample liquid is stored in an optical cell 54 which is a transparent container, as shown in FIG. 13 of the accompanying drawings, and a laser light is applied from a laser source 51 toward. The intensity of transmitted light therethrough is detected by a photodetector 56 and the absorbance thereof is found, and the size and amount of the reacting mixture in the sample liquid are detected, whereby the condensed state of the latex particles can be judged, and the amount of the antigen or antibody which is the object can be quantified.

Figure 14:
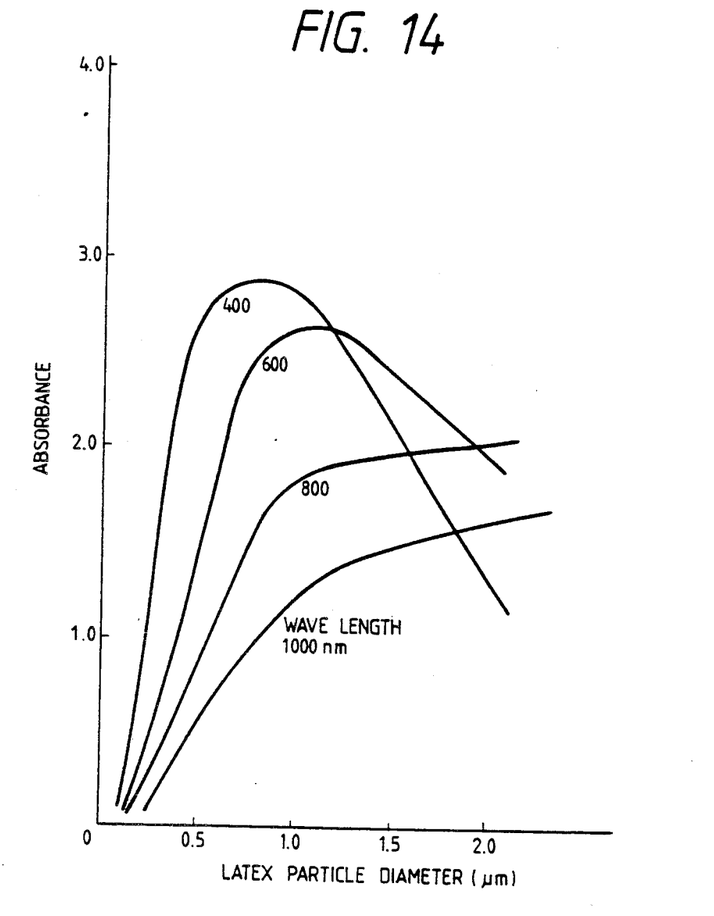
FIG. 14 is a graph showing the relation between latex particle diameter and absorbance.

However, where the size of the condensed lumps of latex particles is to be detected by the absorbance of the latex particle suspension as in the above-described example of the prior art, the absorbance increases linearly as shown in FIG. 14 of the accompanying drawings as the particle diameter of the latex particle lumps becomes larger, but where the wavelength of the irradiating light is a short wavelength such as 400 nm or 600 nm, when the latex particles exceed a predetermined size, the graph of the absorbance is reduced, and two particle diameters correspond to the absorbance found from the intensity of transmitted light, and it has been impossible to judge which particle diameter is right. So, where use is made of a light of such a long wavelength that the graph of the absorbance is not reduced, for example, a light of wavelength 800 nm, if a certain particle diameter (about 1.0 μm) is exceeded, the variation in the absorbance will become small relative to the variation in the particle diameter and measurement sensitivity will become bad.

Therefore, to improve accuracy, it is preferable to prepare a plurality of laser sources of different wavelengths, but as noted previously, this has led to the problems of the bulkiness and expensiveness of the device.

SUMMARY OF THE INVENTION

It is a first object of the present invention to provide a particle measuring device in which the wavelength of irradiating light is converted into the short wavelength side, whereby a light of new wavelength is obtained and a new measurement parameter is obtained.

It is a second object of the present invention to provide a compact and inexpensive particle measuring device which does not require a plurality of light sources to be prepared and can obtain irradiating lights of plural wavelengths.

It is a third object of the present invention to provide a particle measuring device which can use a fluorescent dye which could not heretofore be used.

It is a fourth object of the present invention to provide a particle measuring device which is made compact and inexpensive by using a semiconductor laser as an irradiating light source.

It is a fifth object of the present invention to provide a particle measuring device which can accurately measure the condensed state of the condensed lumps of carrier particles which are the product of immunoreaction, and can measure immunoreaction with good accuracy.

It is a sixth object of the present invention to provide an optical device which, when irradiating lights of plural wavelengths are applied to an object to be irradiated, can correct the chromatic aberration of the irradiating lights of the respective wavelengths and can accomplish the application of the lights to the object to be irradiated under the same condition.

DESCRIPTION OF THE PREFERRED EMBODIMENTS

The present invention uses a nonlinear optical member as light wavelength converting means to thereby make the wavelength of a laser light short. In describing embodiments of the present invention, the nonlinear optical member used in the present invention will first be described.

The nonlinear optical member is a material having a nonlinear optical effect shown in Japanese Patent Application No. 62-51786 and Japanese Patent Application No. 62-54439 previously filed by the applicant.

The nonlinear optical effect used in the present invention uses nonlinear susceptibility expressed by $X^{(n)}(n \geq 2)$ in the nonlinear polarization of a substance shown in equation (1) below.

$$P = \epsilon_0 X^{(1)} E + \epsilon_0 X^{(2)} E^2 + \epsilon_0 X^{(3)} E^3 + \quad (1)$$

What is typical as the nonlinear optical effect using said nonlinear susceptibilities $X^{(1)}, X^{(2)}, X^{(3)}, \ldots, X^{(n)}$ is the light nth harmonic generation. This is a phenomenon, that the light nth harmonic shown by a frequency $n\omega$ $(n \geq 2)$ is generated when a laser light of frequency $\omega$ is applied to a compound having said nonlinear susceptibility $X^{(n)}$. Thus, it becomes possible to make the wavelength of a laser light which is basic short.

What is particularly important in such nonlinear susceptibility includes secondary nonlinear susceptibility $X^{(2)}$ and tertiary nonlinear susceptibility $X^{(3)}$. Among the nonlinear effects using the respective nonlinear susceptibilites, what are applicable to the particle measuring device of the present invention are shown below, and above all, light second harmonic generation (hereinafter referred to as SHG) is excellent in efficiency and SHG is used also in the embodiments of the present invention.

Secondary Nonlinear Susceptibility

Light second harmonic generation (SHG)

$$\omega + \omega \rightarrow 2\omega$$

Sum and difference frequency generation $$\omega_1 \pm \omega_2 \rightarrow \omega_3$$

Light parametric oscillation $$\omega_3 \rightarrow \omega_1 + \omega_2$$

Tertiary Nonlinear Susceptibility

Light third harmonic generation (THG)

$$\omega + \omega + \omega \rightarrow 3\omega$$

Mixing of four light waves $$\omega_1 \pm \omega_2 \pm \omega_3 \rightarrow \omega_4$$

Electric field inducing light second harmonic generation $\omega + \omega + 0 \rightarrow 2\omega$ Mixing of three light waves $\omega_1 - \omega_2 + \omega_3 \rightarrow 107_2 - 2\omega_1$ To cause a laser light to be incident on said nonlinear optical member and effect the conversion of the wavelength of the incident light by the nonlinear optical effect, it is necessary to effect phase adjustment so that the incident basic laser light and the wavelength-converted light may not interfere with each other and be attenuated. Methods of phase adjustment include the following methods, of which a suitable method is selected in conformity with the form of the element.

Figure 4:
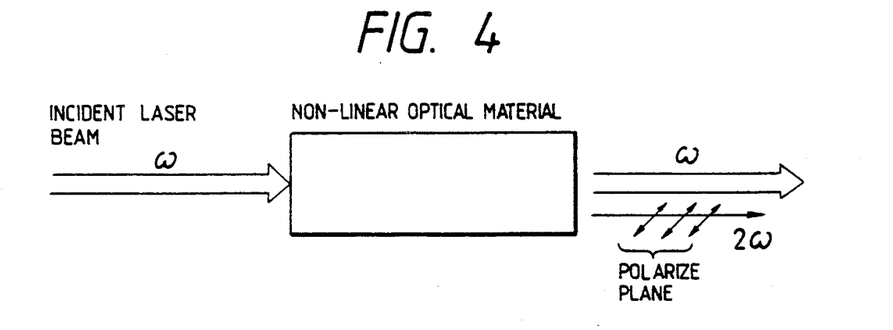
FIGS. 4 to 6 show the construction of a nonlinear optical element.

(a) To use the anisotropy of refractive index in single crystal or bulk material (see FIG. 4)

Figure 5:
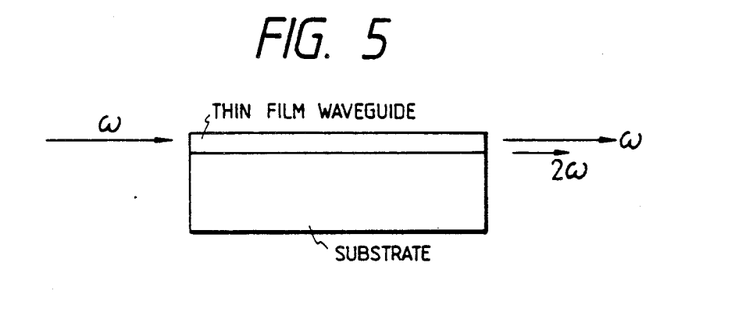

(b) To use the difference in mode in an optical fiber or a light wave guide (see FIG. 5)

Figure 6:
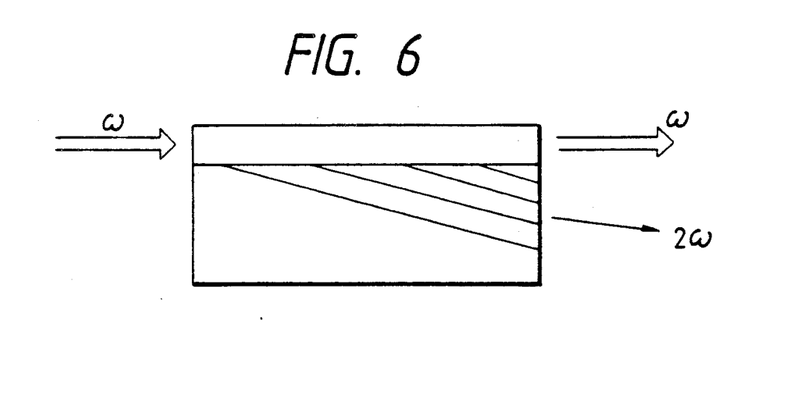

(c) To use cherenkov radiation in an optical fiber or a light wave guide (see FIG. 6)

The element constructed in the manner described above wavelength-converts the basic laser light at the conversion efficiency determined by the laser power density, the phase adjustment length, the nonlinear susceptibility, etc. For example, in the case of SHG, a semiconductor laser (wavelength 830 nm) of the order of 100 mW can be used to obtain conversion efficiency of about 2.5 % for crystal of the order of 1 mm. That is, light second harmonic (wavelength 415 nm) of 2.5 mW is obtained. Also, it is possible to take out the basic laser light which has not been converted at this time simultaneously with said light second harmonic, whereby a laser light of a plurality of wavelengths can be used in the particle measuring device of the present invention.

Where the basic laser light is wavelength-converted by the nonlinear optical effect and the basic laser light and one or more wavelength-converted laser lights are used in the particle measuring device of the present invention, it is possible to apply respective wavelengths $\lambda_1 - \lambda_n$ to the same position and it is also possible to separate the position and apply the respective wavelengths to n locations.

Lasers available in the present invention include a solid laser such as YAG laser (wavelength 1064 $\mu$m), ruby laser (690 nm), $Nd^{3+}$ glass laser (1054-1062 $\mu$m), color center laser or ion-added crystal laser (700-2200 nm), a gas laser such as He-Ne laser (633 nm), Xe laser (2.03 $\mu$m), $Ar^+$ laser (488 or 515 nm), $Kr^+$ laser (647 nm), HF laser (2.6-3.3 $\mu$m) or iodine laser (1.32 $\mu$m), coloring matter laser (0.3-1.6 $\mu$m), semiconductor laser (0.7-1.5 $\mu$m), etc.

When the basic laser light wavelength-converted by the use of the nonlinear optical effect is used, the wavelength of the wavelength-converted laser light is preferably 0.2-1.5 $\mu$m, and more preferably 0.2-0.8 $\mu$m. If said wavelength is less than 0.2 $\mu$m, the nonlinear optical member will be destroyed by light absorption, and if said wavelength is more than 1.5 $\mu$m, it will not be effective in measuring fluorescence. The above-mentioned lasers may be singly used or a combination of two or more of them may be used. Among these lasers, semiconductor laser is easy to modulate and very compact and moderate in cost and therefore is suited for the particle measuring device of the present invention.

Embodiment 1

Figure 1:
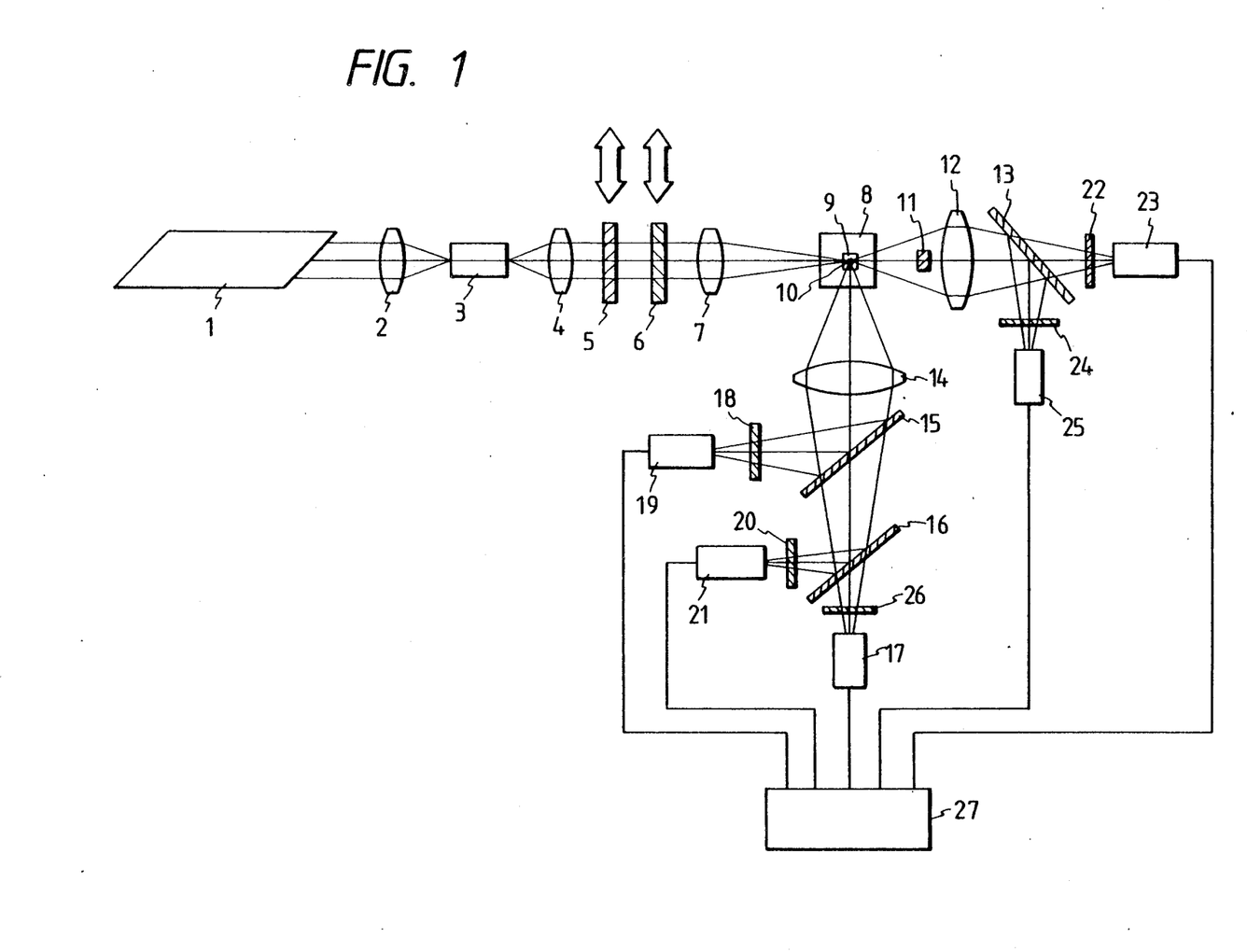
FIG. 1 shows the construction of a first embodiment of the present invention.

A first embodiment of the present invention using the above-described optical member will now be described. FIG. 1 shows the construction of the first embodiment of the present invention in which the basic laser light and a light of light second harmonic can be selected and applied to a particle to be examined.

The basic laser light emitted from a laser source 1 (He-Ne laser of output 100 mW and wavelength 633 nm) is converged by a lens 2 and is caused to be incident on a nonlinear optical member 3 designed for SHG. The reason why the basic laser light is converged and is caused to be incident is that the greater the power density of the incident light, the better the conversion efficiency of the nonlinear optical member will be. Since phase adjustment is done in the nonlinear optical member 3, the basic laser light is converted into a light second harmonic and emerges from the nonlinear optical member 3. At this time, the basic laser light which has not been converted into the light second harmonic also emerges simultaneously. A filter 5 for passing only the basic laser light therethrough and a filter 6 for passing only the light second harmonic therethrough provided in the optical path rearwardly of the nonlinear optical member 3 can be put into and out of the optical path, and one of them is selected to pass only the basic laser light or only the light second harmonic therethrough. At this time, lights of other wavelengths produced by nonlinear optical effects other than SHG, through very slightly, are removed by said filters. By removing the both filters from the optical path, there can be obtained an irradiating light including the two wavelengths of the basic laser light and the light second harmonic. The irradiating light of the selected wavelength is converged by a condensing lens 7 and is applied to a flow cell through-flow portion 9 through which a particle 10 to be examined in a flow cell 8 passes, and scattered light and fluorescence are emitted from the particle 10 to be examined. Direct light which has not been scattered is cut by a stopper 11, and forward scattered light is condensed by a condensing lens 12, and the basic laser light and the light second harmonic are separated from each other by a dichronic mirror 13 transmitting one light therethrough and reflecting the other light, and are received by a set of wavelength selecting filter 22 removing a light of the other wavelength and photodetector 23 and a set of wavelength selecting filter 24 removing a light of the other wavelength and photodetector 25, respectively.

Also, in order to obtain the information of the particulate property of the particle to be examined from sideways scattered light, the sideways scattered light (the basic laser light and the light second harmonic) passed through a condensing lens 14 and dichroic mirrors 15 and 16 is intensity-detected by a set of wavelength selecting filter 26 and photodetector 17. The wavelength selecting filter 26 is a filter for selecting one of the basic laser light and the light second harmonic, and if this filter 26 is retracted out of the optical path, the basic laser light and the light second harmonic can both be detected. The dichroic mirrors 15 and 16 transmit the sideways scattered light (the basic laser light and the light second harmonic) therethrough and reflects fluorescence (fluorescence corresponding to the basic laser light and fluorescence corresponding to the light second harmonic).

Further, in order to dye the particle to be examined with a fluorescent dye and receive the fluorescence emitted from the particle to be examined excited by the irradiating light and know the cytochemical property thereof, the intensity of the fluorescence is detected by an optical system constituted by the dichroic mirror 15, a wavelength selecting filter 18 for wavelength-selecting only the fluorescence corresponding to the basic laser light and a photodetector 19, and the intensity of fluorescence of another wavelength is detected by an optical system constituted by the dichroic mirror 16, a wavelength selecting filter 20 capable of selecting only the fluorescence corresponding to the light second harmonic and a photodetector 21.

As a modification of the optical system for photometering the fluorescence, a combination of continuous spectral means such as a prism and an array sensor such as a CCD as shown in Japanese Laid-Open Patent Application No. 61-17314 can be adopted instead of a combination of a dichroic mirror, a wavelength selecting filter and a photodetector to thereby detect the fluorescence in a continuous wavelength component and obtain more detailed measurement data.

The detection signals of the photodetectors 23, 25, 17, 19 and 21 are input to a calculation circuit 27, where the calculation of particle analysis is effected. The method of calculation of particle analysis is widely known from literature and numerous patents and therefore need not be described in detail herein.

In the present embodiment, a single basic laser light is used and an irrading light of two wavelengths is obtained by the nonlinear optical member, but two or more basic laser lights of different wavelengths may be caused to be incident on the nonlinear optical member at a time to thereby obtain an irradiating light including lights of plural wavelengths. In such case, the lights of plural wavelengths obtained are wavelength-selected by the selection of a group of wavelength selecting filters provided for the separation of the wavelengths and are applied to the portion to be examined.

Figure 2:
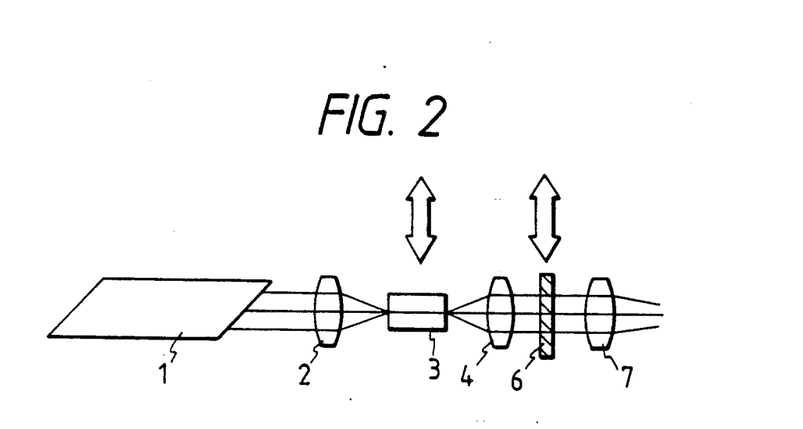
FIG. 2 shows an irradiating optical system according to a modification of the first embodiment.

As a modification of the present embodiment, the optical arrangement of the irradiating system is shown in FIG. 2. As compared with FIG. 1, the filter 5 for passing only the basic laser light therethrough is omitted and the nonlinear optical member 3 can be put into and out of the optical path. By putting the nonlinear optical member 3 into the optical path and removing the filter 5 from the optical path, both the basic laser light and the light second harmonic are obtained, and by putting both members into the optical path, only the light second harmonic is obtained. Also, by removing the both members from the optical path, only the basic laser light is obtained.

Embodiment 2

Figure 3:
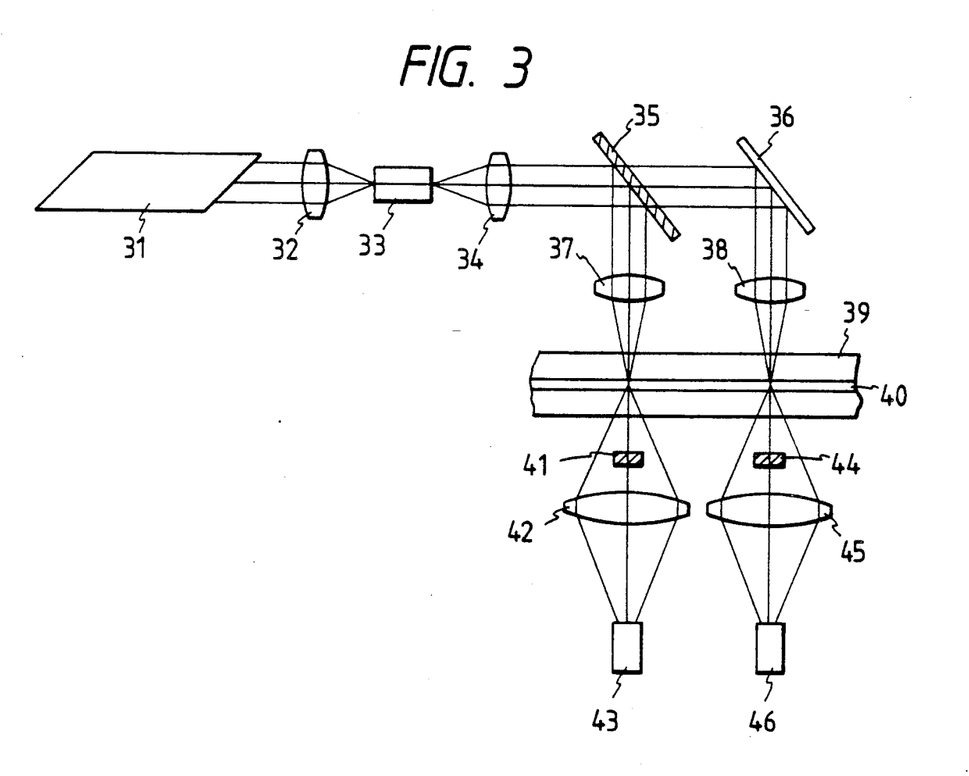
FIG. 3 shows the construction of a second embodiment of the present invention.

FIG. 3 shows a second embodiment of the present invention in which the basic laser light and the light second harmonic are separated from each other and the two wavelength are applied to the particle to be examined at discrete positions.

The basic laser light is emitted from a laser source 31 (semiconductor laser of output 100 mW and wavelength 780 nm), and is converged by a condensing lens 32 and is caused to be incident on a nonlinear optical member 33 designed for SHG. The light second harmonic generated with the basic wave is separated by a dichroic mirror 35, and this light second harmonic is applied by an optical system 37 to a flow cell through-flow portion 40 through which the particle to be examined in the flow cell 39 passes. Further, the basic wave passed through the dichroic mirror 35 is reflected by a total reflection mirror 36, and is applied to the flow cell through-flow portion 40 by an optical system 38 which is spaced apart by the order of 200 μm from the optical system 37 in its application position to the flow cell through-flow portion 40. The direct light is cut by stoppers 41 and 44, and the forward scattered lights from the particle to be examined are discretely detected by a set of light receiving lens 42 and photodetector 43 and a set of light receiving lens 45 and photodetector 46. Also, sideways scattered light and fluorescence are detected by two discrete sets of sideways optical systems, not shown. These detected signals are input to a calculation circuit, not shown, where the calculation of particle analysis is effected.

Figure 7:
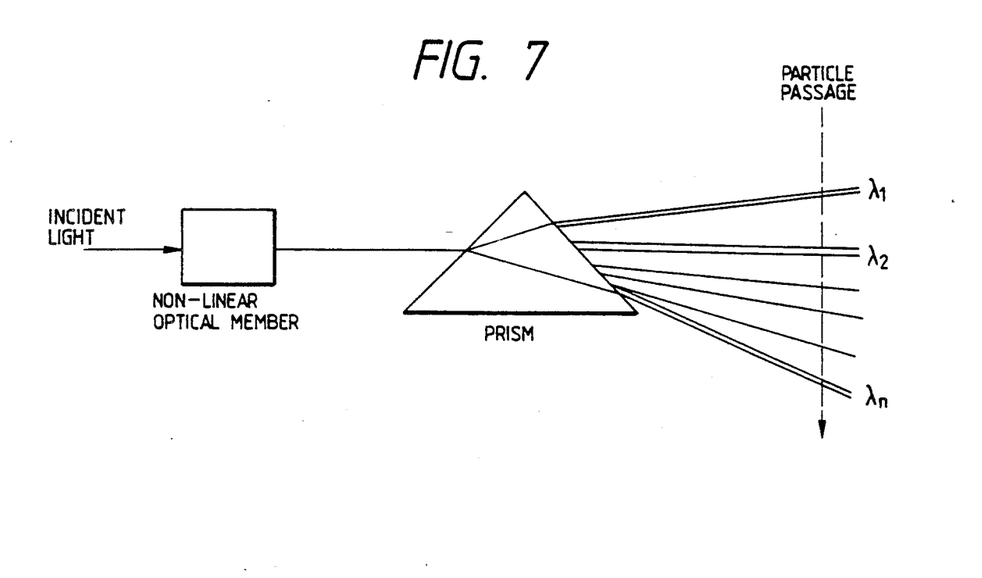
FIGS. 7 and 8 illustrate a method of separating a plurality of wavelengths and applying them to a flow portion.
Figure 8:
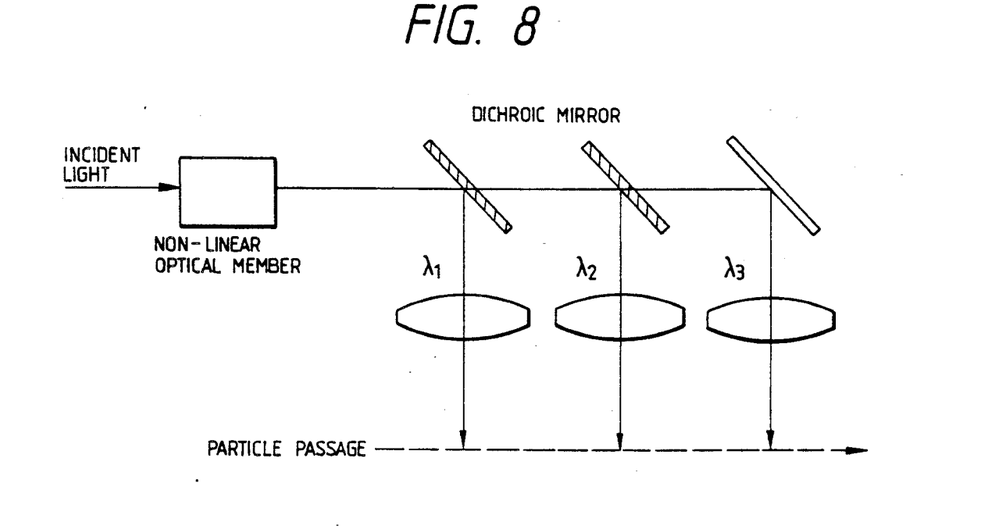

In the present embodiment, a single laser source is prepared and an irradiating light of two wavelengths is obtained by the nonlinear optical member, but it is also possible to cause two or more basic laser lights of different wavelength to be incident on the nonlinear optical member at a time, and obtain an irradiating light including lights of plural wavelengths. In such case, the lights of different wavelengths can be separated from each other by a method as shown in FIG. 7 or 8 and applied to the flow cell through-flow portion.

As described above, the incident light is wavelength-converted into the short wavelength side by the use of the nonlinear optical member, whereby a long wavelength laser such as semiconductor laser or YAG laser which could heretofore not be utilized because of its too long wavelength for excitation of fluorescence becomes usable, and an irradiating light of new wavelength which has heretofore not been available can be obtained by making the He-Ne laser or the like heretofore used into a half-wavelength. As a result, measurement parameters increase and it becomes possible to improve the analysis accuracy and the amount of analysis information.

For example, by making the semiconductor laser into a half-wavelength, a fluorescent dye which could heretofore not been used, such as 9-aminoacridine (excitation wavelength 400 nm and fluorescence wavelength 454 nm) or 12 (9-anthroyloxy) stearic acid (excitation wavelength 386 nm and fluorescence wavelength 464 nm) can be used and therefore, particle information which could heretofore not be obtained becomes measurable. Also, conversely, this greatly contributes to the development of new fluorescent dyes.

Further, heretofore, the irradiating light used for the excitation of fluorescence has been a single wavelength and therefore, the fluorescent dye used for the dyeing of the particle to be examined in one measurement has been limited to one kind or a combination of kinds in which the fluorescence wavelength distributions do not overlap each other. However, according to the present invention, the irradiating light for the excitation of fluorescence can be a plurality of wavelengths and therefore, a plurality of fluorescent dyes differing in excitation wavelength can be freely combined, and by receiving a plurality of fluorescences at a time, the analyzing power can be greatly improved. For example, in the first embodiment using He-Ne laser, 3,3'-dipropyl-thiadicarbocyanine (excitation wavelength 622 nm and fluorescence wavelength 670 nm) and β(9,11,13,15-all-trans) octadecatetraenoic acid (excitation wavelength 314 nm and fluorescence wavelength 422 nm) can be used to dye the particle to be examined in advance with these two kinds at a time, whereby the two can be measured at a time.

Embodiment 3

Figure 9A:
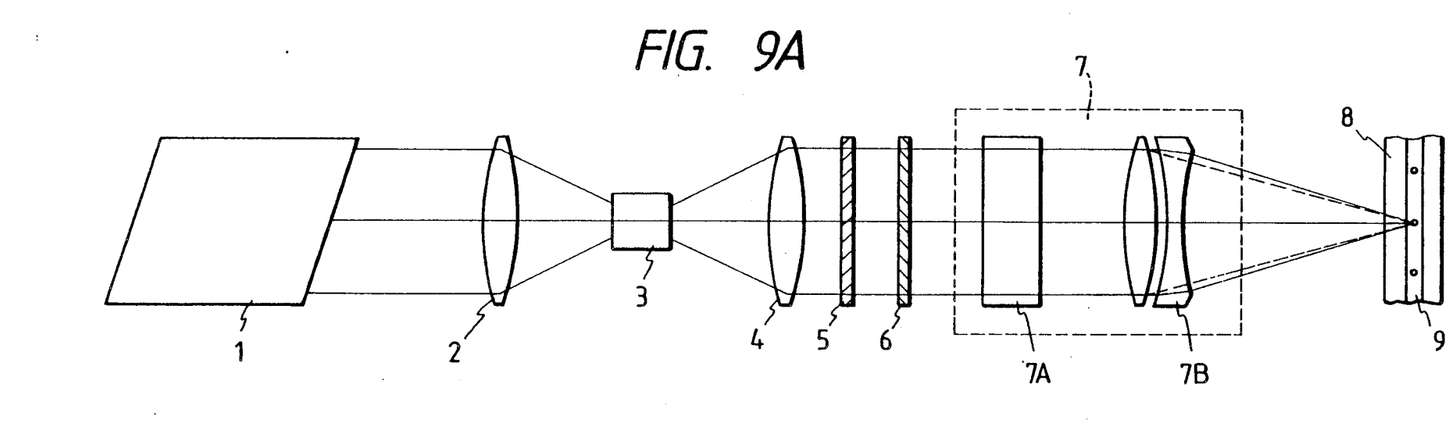
FIGS. 9A and 9B show the construction of an irradiating optical system according to a third embodiment of the present invention.
Figure 9B:
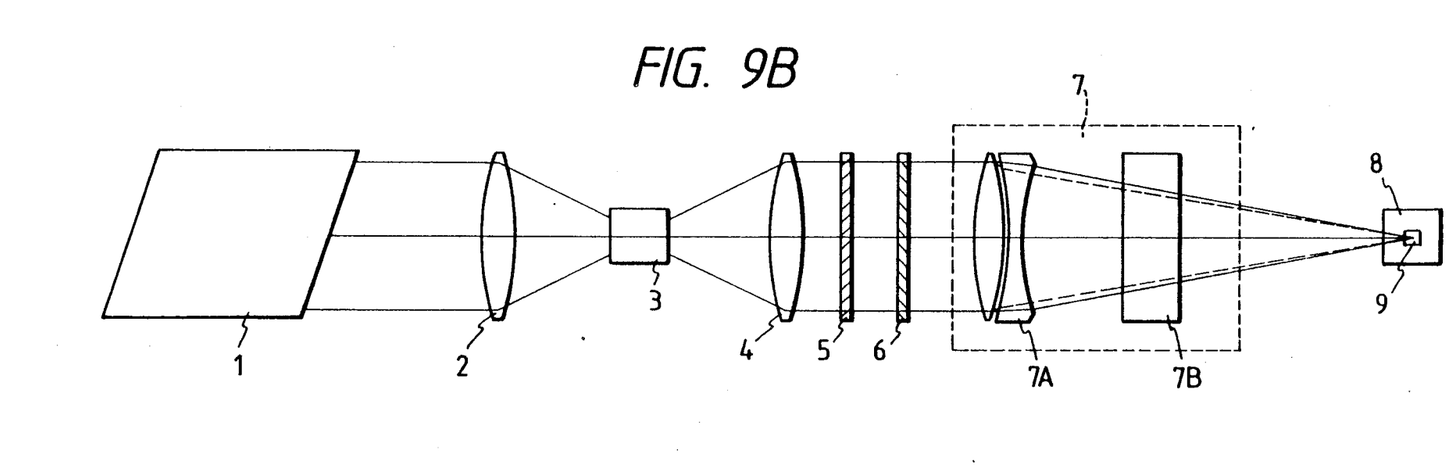

A third embodiment of the present invention provided with a more improved light applying optical system will now be described with reference to FIGS. 9A and 9B. FIG. 9A is a side view of the optical system, and FIG. 9B is a view of the optical system as seen in the vertical direction. The construction of FIG. 9 is the same as that of FIG. 1 except for the imaging lens unit 7, and similar reference numerals designate similar members.

Figure 10:
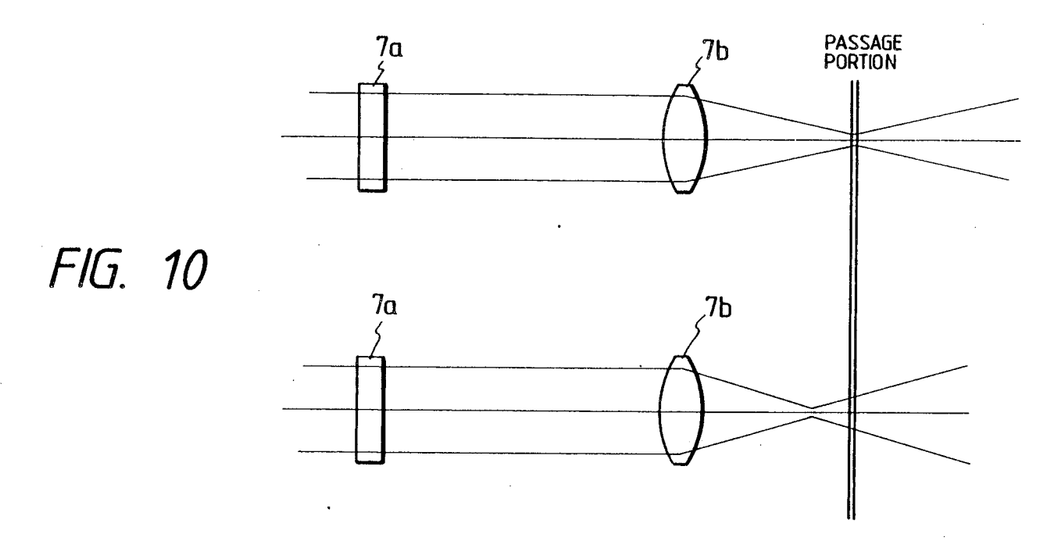
FIG. 10 illustrates chromatic aberration.

In the above-described embodiments, the problem of chromatic aberration is not taken into consideration, and there has been the problem that if the wavelength of the light differs, the refractive index n differs even for the same lens and accordingly the focal length also differs and the phenomenon of chromatic aberration that the position at which the light is converged differs as shown in FIG. 10 arises. So, the present invention uses achromatic cylindrical lenses to effect achromatization which eliminates this chromatic aberration and thereby solve this problem.

In FIGS. 9A and 9B, the convergence of both the basic laser light $\lambda_a$ and the light second harmonic $\lambda_b$ in a direction orthogonal to the direction of particle flow is accomplished by an achromatic cylindrical lens 7A, and the convergence thereof in the direction of particle flow is accomplished by an achromatic cylindrical lens 7B. The achromatic cylindrical lenses 7A and 7B are both designed such that at this time, the beam waists of the basic laser light $\lambda_a$ and the light second harmonic $\lambda_b$ are positioned at the flow cell through-flow portion 9.

To make a lens free of chromatic aberration, a positive and a negative lens must be combined together. The positive and negative lenses ($f_1 > 0$, $\nu_1$: $f_2 < 0$, $\nu_2$) may preferably be as great as possible in the difference between dispersive powers $\nu_1$ and $\nu_2$. The term "dispersive power" used herein is an amount indicative of the ability with which a substance disperses light, and it differs from substance to substance. In practical use, a combination of crown and fliut glass is often used with weight and corrosion resistance taken into account, and if a parallel light beam is incident on it, the refracting actions of concave and convex lenses negate each other and lights of different wavelengths $\lambda_a$ and $\lambda_b$ converge at a point.

By using the cylindrical lenses 7A and 7B in which achromatization has been effected by such a method, both of on-axis chromatic aberration and chromatic difference of magnification can be corrected and the beam waists of the basic laser light $\lambda_a$ and the second harmonic $\lambda_b$ thereof can both be converged at the same position in the flow cell through-flow portion.

The laser unit and the achromatic optical system need not always be disposed separately from each other, but a similar optical system may be incorporated into the laser unit.

According to the present embodiment, the basic laser light or the second harmonic thereof is converged at the flow cell through-flow portion by the use of cylindrical lenses taking achromatism into account, whereby the beam waists can be positioned at the sample part of the through-flow portion in the same optical path by the same lens and therefore, the loss of the quantity of applied light is null and the measurement accuracy is improved and further, it becomes unnecessary to effect fine adjustment each time the wavelength of the light used for irradiation is changed.

Embodiment 4

Figure 11:
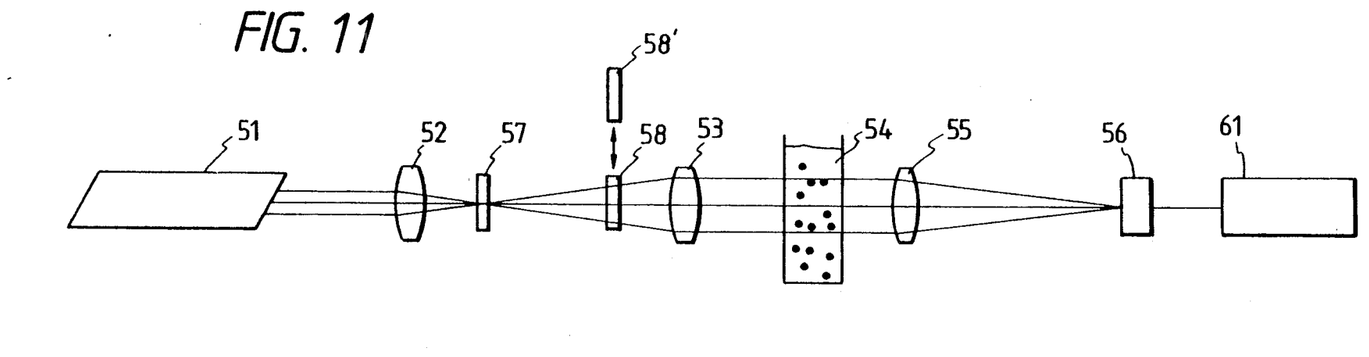
FIG. 11 shows the construction of a fourth embodiment of the present invention.

FIG. 11 shows the construction of a fourth embodiment of the present invention, and a laser light emitted from a semiconductor laser source 51 of wavelength 800 nm is applied to a nonlinear optical member 57 disposed at the focus position of a condensing lens 52. The reason why the nonlinear optical member 57 is disposed at the focus position which is high in energy density is that the higher the energy density of the applied light, the higher the wavelength converting efficiency of the nonlinear optical member will be. The light made into a half-wavelength, that is, converted into 400 nm, by the SHG effect of the nonlinear optical member 57 in conformity with the converting efficiency follows the same optical path as the original light of wavelength 800 nm which has not been converted. A filter 58 transmitting only a light of wavelength 800 nm therethrough and a filter 58' transmitting only a light of wavelength 400 nm therethrough disposed rearwardly of the nonlinear optical member 57 are adapted to be successively changed over by a mechanism, not shown, and disposed in the optical path, whereby the lights of wavelengths 800 nm and 400 nm are successively selected. The lights of the selected wavelengths pass through a condensing lens 53 and are applied to a latex suspension of a predetermined concentration stored in an optical cell 54. At this time, the lights transmitted through the latex suspension in the optical cell 54 have their transmitted light intensities detected by a photodetector 56. The transmitted light intensities are detected correspondingly to the irradiating lights of wavelengths 800 nm and 400 nm successively applied, and the detection outputs are input to a calculation circuit 61.

As regards the measurement of the transmitted lights, both of one measurements and continuously repeated measurement are possible and therefore, this can cope with any of reaction speed analyzing method and the reaction terminal analyzing method.

The latex suspension, as shown in FIG. 14, differs in absorbance characteristic between a case where the light of wavelength 800 nm is used as the irradiating light and a case where the light of wavelength 400 nm is used as the irradiating light, and by measuring the transmitted light intensities at the two wavelengths and calculating the absorbance, two different measurement data are obtained. Description will hereinafter be made of a method of finding the average particle diameter of condensed latex lumps in the suspension from these two data of absorbance.

Referring to FIG. 14, the absorbance characteristic of the light of wavelength 800 nm monotonously increases up to the absorbance of about 1.8 and the latex particle diameter of about 1.0 $\mu$m, but the increase in absorbance becomes almost null if the latex particle diameter exceeds about 1.0 $\mu$m. That is, if the absorbance obtained for the irradiating light of wavelength 800 nm is of the order of 1.8-2.0, accurate calculation of the latex particle diameter is difficult. Also, the absorbance characteristic of the light of wavelength 400 nm becomes maximum for the absorbance of about 2.8 and the latex particle diameter of 0.7 $\mu$m, whereafter its inclination reverses. That is, there are two latex particle diameters corresponding to the absorbance obtained for the irradiating light of wavelength 400 nm and therefore, a right latex particle diameter cannot be specified. It is difficult to specify an accurate latex particle diameter from one kind of absorbance thus obtained by an irradiating light of one wavelength.

However, an accurate latex particle diameter can be found by referring to two data obtained by irradiating lights of two different wavelengths. The absorbance for the wavelength 800 nm is first referred to and if the absorbance is smaller than 1.8, that is, if the latex particle diameter is smaller than 1.0 μm, the then latex particle diameter for the absorbance for the wavelength 400 nm or 800 nm is the latex particle diameter sought after. In this case, the absorbance for any of the two wavelengths may be used. Also, if the absorbance for the wavelength 800 nm is greater than 1.8, that is, if the latex particle diameter is greater than 1.0 μm, the absorbance for the wavelength 400 nm is referred to and the corresponding latex particle diameter is found.

By thus using the portion of the absorbance graph which is high in measurement sensitivity, a highly accurate latex particle diameter can be calculated and therefore, highly accurate immunity measurement becomes possible.

Embodiment 5

Figure 12:
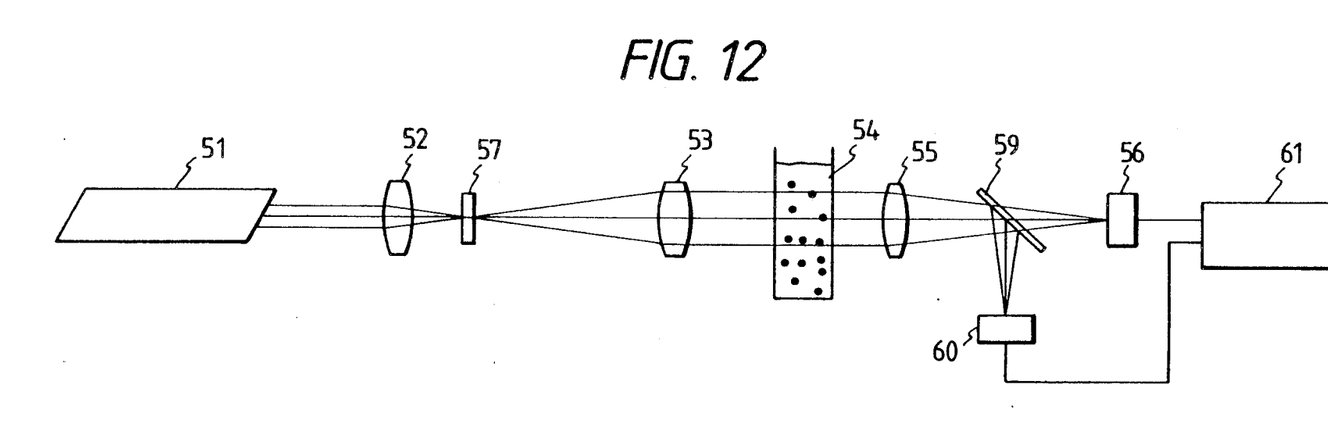
FIG. 12 shows the construction of a fifth embodiment of the present invention.

FIG. 12 shows the construction of a fifth embodiment of the present invention. In FIG. 12, reference numerals similar to those in FIG. 11 designate similar members.

In contrast with the previous fourth embodiment, the present embodiment is designed such that lights of two wavelengths are applied to sample liquid at a time and the transmitted light intensities are independently detected for the respective wavelengths, and the filter change-over mechanism in Embodiment 4 is unnecessary. A dichroic mirror 59 is provided in the optical path of the light receiving optical system rearward of an optical cell 54, and the transmitted light of wavelength 800 nm is transmitted through the dichroic mirror 59 and is received by a photodetector 56. Also, the transmitted light of wavelength 400 nm reflected by the dichroic mirror 59 is received by a photodetector 60. The outputs of the photodetectors 56 and 60 are input to a calculation circuit 61.

By using two kinds of absorbances thus obtained, an accurate latex particle diameter can be found in the same manner as in the previous embodiment.

Embodiment 6

In Embodiments 4 and 5, the average particle diameter has been calculated from the intensity of the light transmitted through the suspension, but a method of analyzing the latex suspension and immunity-measuring by the use of the previously described device of FIG. 1 or 3 is conceivable as another method. A method of causing a latex particle or a lump of latex particles to flow by a sheath flow system by the use of a flow cytometer, discriminating the particle size, i.e., the condensed state, of the individual latex particles from the intensity of the photometered scattered light, and effecting the measurement of the reaction of an antigen or an antibody is known. By measuring the intensities of the respective scattered lights for a plurality of irradiating lights with respect to the individual latex particles in the latex suspension by the use of the device of FIG. 1 or 3, a plurality of particle diameter data can be obtained and a more accurate particle size can be found. Thereby, immunity measurement of higher accuracy than the prior art becomes possible.

In all the above-described embodiments, the SHG effect of the nonlinear optical member is utilized, but by using a nonlinear optical member designed for THG, it is also possible to obtain an irradiating light having ⅓ of the wavelength of the basic wave.

Further, the number of the wavelengths used is not limited to two, but by using three or more wavelengths, it is possible to attain a further improvement in accuracy. Also, a plurality of converted wavelengths may of course be used instead of the wavelength of the basic laser light.

Furthermore, the basic laser light used is not limited to that shown in the embodiments, but a laser suited for the purpose of measurement may be selected and used.

The laser source and the wavelength converting means need not always be discretely disposed in the optical path as in the embodiments, but if use in made of a laser unit incorporating the wavelength converting means in the laser source, accurate alignment and focusing adjustment of the laser source and the wavelength converting means will become unnecessary.

The wavelength converting means used need not always be a nonlinear optical member as in the embodiments, but may also be a member having the wavelength converting property, such as a Raman cell.

What is claimed is:

1. A particle measuring device for measuring multiple-dyed particles, comprising:

light source means including a laser source for generating an initial light beam having a predetermined wavelength;

a nonlinear optical member having a nonlinear optical effect, said nonlinear optical member converting the initial light beam into a first light beam having a first wavelength and a second light beam having a second wavelength;

projection means having a changeover means for selecting at least one of said first light beam and second light beam and for projecting the selected light beam to the particles dyed with a plurality of fluorescent dyes;

light receiving means for receiving a plurality of light beams having different wavelengths from the particles; and calculation means for analyzing characteristics of the particles on the basis of output of said light receiving means.

2. A particle measuring device according to claim 1, wherein said changeover means includes a wavelength selection filter.

3. A particle measuring device according to claim 1, wherein said changeover means includes first and second wavelength selection filters for selecting said first and second wavelengths, with said first and second filters being independently and selectively provided within a light path.

4. A particle measuring device according to claim 1, wherein said projection means comprise an optical system for compensating for a chromatic aberration of said first and second light beams generated by said nonlinear optical member.

5. A particle measuring device according to claim 1, wherein said light receiving means receives at least one of a scattered light and a fluorescence emitted from the particles.

6. A particle measuring device according to claim 1, further comprising flow cell means for transporting the particles one by one in a sheath flow, and wherein said projected light beam is projected to the particles at a portion in said flow cell means.

7. A particle measuring device according to claim 1, wherein said nonlinear optical effect is an SHG effect.

8. A particle measuring device according to claim 1, wherein said first wavelength is said predetermined wavelength and said second wavelength is said wavelength converted into the short wavelength side.

9. A particle measuring device according to claim 1, wherein said light source means includes a semiconductor laser.

10. A particle measuring device for measuring multiple dyed particles, comprising:
light source means including a laser source for generating an initial light beam having a predetermined wavelength;
a nonlinear optical member having a nonlinear optical effect, said nonlinear optical member converting the initial light beam into a first light beam having a first wavelength and a second light beam having a second wavelength;
projection means for projecting said first light beam and said second light beam to particles dyed with a plurality of fluorescent dyes;
first light receiving means for receiving a plurality of fluorescent lights generated by excitation of the particles; and
calculation means for analyzing characteristics of the particles on the basis of output of said light receiving means.

11. A particle measuring device according to claim 10, further comprising second light receiving means for receiving light scattered by the particles.

12. A particle measuring device according to claim 10, wherein said nonlinear optical effect is an SHG effect.

13. A particle measuring device according to claim 10, wherein said first wavelength is said predetermined wavelength and said second wavelength is said wavelength converted into the short wavelength side.

14. A particle measuring device according to claim 10, wherein said light source means includes a semiconductor laser.

15. A particle measuring device according to claim 10, further comprising flow cell means for transporting the particles one by one in a sheath flow, and wherein said projected light beam is projected to the particles at a portion in said flow cell means.

16. A particle measuring device according to claim 10, wherein said light projection means includes an optical system for compensating for a chromatic aberration of said first and second light beams generated by said nonlinear optical member.

17. A particle measuring device according to claim 10, wherein said projected light beam is projected to particles that are living cells.

18. A particle measuring device for measuring carrier particles in a reaction liquid including immunoreaction fluid, comprising:
light source means including a laser source for generating an initial light beam having a predetermined wavelength;
a nonlinear optical member having a nonlinear optical effect, said nonlinear optical member converting the initial light beam to a first light beam having a first wavelength and a second light beam having a second wavelength;
projection means for projecting said first light beam and said second light beam tot he reaction liquid;
light receiving means for receiving a scattered light or a transmitted light from said first wavelength light beam and a scattered light or a transmitted light from said second wavelength light beam; and
calculation means for measuring the immunoreaction by discriminating the condensed state of the carrier particles on the basis of the two detected values obtained by said light receiving means.

19. A particle measuring device according to claim 18, wherein said nonlinear optical effect is an SHG effect.

20. A particle measuring device according to claim 18, wherein said first wavelength is said predetermined wavelength and said second wavelength is said wavelength converted into the short wavelength side.

21. A particle measuring device according to claim 18, wherein said light projection means includes an optical system for compensating for a chromatic aberration of said first and second light beams generated by said nonlinear optical member.

22. A particle measuring device according to claim 18, wherein said light source means includes a semiconductor laser.

23. A particle measuring device according to claim 18, wherein said projected light beam is projected to carrier particles that are latex particles.

24. A particle measuring device according to claim 18, wherein said projected light beam is projected to carrier particles that include a monoclonal antibody which peculiarly reacts with an object antigen and is sensitized at a surface of the carrier particles.

25. A particle measuring device according to claim 18, further comprising an optical cell for containing the reaction liquid.

26. A particle measuring device according to claim 18, further comprising flow cell means for transporting the particles one by one in a sheath flow, and wherein said projected light beam is projected to the particles at a portion in said flow cell means.

27. A light projection unit for use with a multiple-dyed particle measuring device, comprising:
light source means including a laser source for generating an initial light beam having a predetermined wavelength;
a nonlinear optical member having a nonlinear optical effect, said nonlinear optical member converting the initial light beam to a first light beam having a first wavelength and a second light beam having a second wavelength; and
projection means having changeover means for selecting at least one of said first light beam or said second light beam and for projecting the selected light beam to a particle dyed with a plurality of fluorescent dyes.

28. A light projection unit according to claim 27, wherein said changeover means includes a wavelength selection filter.

29. A light projection unit according to claim 27, wherein said changeover means includes first and second wavelength selection filters for selecting said first and second wavelength, and said first and second filters are independently and selectively provided within a light path.

30. A light projection unit according to claim 27, wherein said projection means comprises an optical system for compensating for a chromatic aberration of said first and second light beams generated by said nonlinear optical member.

31. A light projection unit according to claim 27, wherein said nonlinear optical effect is an SHG effect.

32. A light projection unit according to claim 27, wherein said first wavelength is said predetermined wavelength and said second wavelength is said wavelength converted into the short wavelength side.

* * * * *

UNITED STATES PATENT AND TRADEMARK OFFICE
CERTIFICATE OF CORRECTION

PATENT NO. : 5,123,731

DATED : June 23, 1992

INVENTOR(S) : Kazuo Yoshinaga, et al.

It is certified that error appears in the above-identified patent and that said Letters Patent is hereby corrected as shown below:

On the Title page, item

[57] ABSTRACT:

Line 3, "examined," should read --examined, a--.
Line 4, "a" should be deleted.

COLUMN 2:

Line 48, "toward" should read --toward it.--.

COLUMN 5:

Line 6, "$\omega_1-\omega_2+\omega_3 \rightarrow 107\ _2-2\omega_1$" should read --$\omega_1-\omega_2+\omega_3 \rightarrow \omega_2-2\omega_1$--.

COLUMN 11:

Line 6, "two" should be deleted.

COLUMN 12:

Line 17, "in" should read --is--.

COLUMN 13:

Line 13, "ple dyed" should read --ple-dyed--.
Line 59, "immunoreaction" should read --immuno-reaction--.

UNITED STATES PATENT AND TRADEMARK OFFICE
CERTIFICATE OF CORRECTION

PATENT NO. : 5,123,731

DATED : June 23, 1992

INVENTOR(S) : Kazuo Yoshinaga, et al.

It is certified that error appears in the above-identified patent and that said Letters Patent is hereby corrected as shown below:

COLUMN 14:

Line 2, "tot he" should read --to the--.
Line 7, "immunoreaction" should read --immuno-reaction--.

Signed and Sealed this

Twenty-eighth Day of September, 1993

Attest:

BRUCE LEHMAN

Attesting Officer     Commissioner of Patents and Trademarks